United States Patent [19]

Shaw et al.

[11] 4,453,006

[45] Jun. 5, 1984

[54] OXIDATION OF PROPYLENE OR ISOBUTYLENE WITH ATTRITION RESISTANT CATALYSTS

[75] Inventors: Wilfrid G. Shaw, Lyndhurst; Christos Paparizos, Cleveland; James L. Callahan, Wooster, all of Ohio

[73] Assignee: The Standard Oil Company, Cleveland, Ohio

[21] Appl. No.: 233,742

[22] Filed: Feb. 12, 1981

Related U.S. Application Data

[62] Division of Ser. No. 76,115, Sep. 17, 1979, Pat. No. 4,280,929.

[51] Int. Cl.$^3$ .................. C07C 45/35; C07C 47/22; C07C 51/25; C07C 57/05
[52] U.S. Cl. .................. 562/545; 562/532; 562/534; 562/535; 562/546; 562/547; 568/476; 568/477; 568/479; 568/480; 502/200; 502/255

[58] Field of Search ............... 562/545, 547, 546, 532, 562/534, 535; 568/476, 477, 479, 480; 252/456, 458, 439, 437, 435

[56] References Cited

U.S. PATENT DOCUMENTS 4,148,757  4/1979  Brazdil et al. ................ 252/437
4,170,570 10/1979  Zagata ........................... 252/437
4,177,158 12/1979  Blue .............................. 252/437

*Primary Examiner*—Vivian Garner
*Attorney, Agent, or Firm*—Debra L. Pawl; David J. Untener; Larry W. Evans

[57] ABSTRACT

A method for preparing attrition resistant, high percentage active component catalysts comprises using two types of silica, one of which is fumed silica, in a two stage catalyst preparation.

3 Claims, No Drawings

OXIDATION OF PROPYLENE OR ISOBUTYLENE WITH ATTRITION RESISTANT CATALYSTS

This is a division of application Ser. No. 76,115 filed Sept. 17, 1979, now U.S. Pat. No. 4,280,929.

BACKGROUND OF THE INVENTION

The present invention relates to a multi-component oxide catalyst. Catalysts of this type are known to be useful in the oxidation of olefins to oxygenated hydrocarbons, oxidation of olefin-ammonia mixtures to unsaturated nitriles and oxidative dehydrogenation of monoolefins to diolefins. Examples of these reactions are the oxidation of propylene to acrolein, isobutylene to methacrolein, acrolein to acrylic acid, propylene and ammonia to acrylonitrile, and butene-1 or butene-2 to butadiene.

Examples of such catalysts may be found in U.S. Pat. Nos. 3,642,930, 3,773,692, 4,042,533 and 3,956,181. Basically, the present invention applies to any supported oxide catalyst utilized in the above reactions.

These catalysts are normally supported on some form of carrier to improve their physical properties. Typical carriers have included silica, titania, alumina and silicon carbide. The carriers are generally inert, but can be in the active form.

U.S. Pat. No. 4,092,354 discloses a conventional method of preparing a supported oxide catalyst. First, the required elements in the form of nitrates, etc., are dissolved in water. The carrier is then added, the mixture evaporated and calcined. The catalyst may be formed and calcined prior to carrier addition, as shown in U.S. Pat. Nos. 3,992,419 and 4,075,127.

Of the carriers noted above, silica has been one of the more frequently used supports. U.S. Pat. No. 4,092,354 discloses the use of silica sol, silica jel or silica containing diatomaceous earth. U.S. Pat. No. 3,773,692 discloses the use of fumed silica (silicon dioxide) along with one or more components having a small specific surface area. This combination of surface area carriers is used to control the activity of the catalyst.

It has been discovered that the use of fumed silica in the first step of a two-step catalyst preparation, followed by the addition of a standard high surface area silica compound in the second step, results in a catalyst having better physical strength for a fluid bed or transfer line operation and greater activity and selectivity than the prior art supported catalyst.

SUMMARY OF INVENTION

The present invention may be considered a process for preparing a supported, solid oxide complex catalyst comprising the steps of:

(a) adding fumed silica to a mixture containing one or more active components of the catalyst;

(b) drying said mixture to form a dried firststage mixture;

(c) adding in solution a member selected from the group of silica and a silica-containing compound other than fumed silica to said dried mixture of (b);

(d) drying and calcining said mixture of (c).

Fumed silica is a very fine silica that can be produced by reacting silicon tetrachloride with hydrogen and oxygen in a flame. A description of fumed silica can be found in the *Encyclopedia of Chemical Technology*, 2nd. Ed., Kurt Othmer, Vol. 18, page 63. Fumed silica may be purchased under the tradename Aerosil or Cabosil.

In the first stage of catalyst preparation, the fumed silica is mixed with one or more of the active components of the catalyst. Methods of combining the required active elements of the catalysts are well known in the art and need not be described in detail. The present invention is applicable to the majority if not all of the various methods utilized as long as the silica can be added in two distinct stages, with fumed silica being used initially.

The starting materials used to add the particular active elements to the oxide catalyst can be those conventionally employed in the art. Active components are defined as the oxides of the active elements or the reagents used to form the oxides. Normally, decomposable salts which will yield the desired elements upon heating to elevated temperatures are employed, although oxides and even free acids can be used. Other reagents include nitrates, carbonates, chlorides, and organic acid salts.

Various procedures that have been developed for catalyst preparation, such as pH control or refluxing are well known in the art and can also be used when preparing the present invention's catalyst.

At least one active component must be present in the first stage. Though all of the active components can be utilized in the first stage, part of the active composition can also be added during the second stage preparation with the additional silica. This two-step preparation of active components is similar to the process found in Ser. No. 823,319, filed Aug. 10, 1977, now U.S. Pat. No. 4,148,757, disclosing a method for preforming a molybdenum-oxide catalyst.

While the present invention is applicable to a solid oxidation catalyst containing any known elements, it is preferred that the invention be utilized with those catalysts containing molybdenum. It is also preferred that the active components in the first stage contain molybdenum, bismuth-molybdenum, antimony-molybdenum, or tellurium-molybdenum as the minimum elements present. The source of molybdenum may be, for example, molybdenum oxide dissolved in an aqueous ammonium hydroxide solution, ammonium heptomolybdate, or molybdic acid. Preferred is the use of the ammonium hydroxide solution or ammonium heptomolybdate.

The fumed silica should be well mixed with the active components in a slurry or solution before proceeding to the drying step. It is believed that the better dispersion of the fumed silica at this stage, the better the attrition resistance of the catalyst.

The amount of fumed silica added can be 5–95% of the total silica used with 15–65% being preferred. An advantage of the present invention is that attrition-resistant catalyst containing significantly lower percentages of silica than previously used can be prepared. This leads to a more active catalyst while still retaining good physical properties.

After the fumed silica has been added, the slurry or solution is then dried. This drying can be by simple heat treatment, but it is preferred to use spray drying for fluid-bed catalysts. Other forms of drying, such as evaporation or double-drum drying may also be used.

After drying, the first stage may be calcined to form the active phase of the catalyst. Calcining at temperatures between 200°–700° C., preferred being 400°–600° C. can be accomplished after either or both steps of the catalyst preparation. If, for example, all of the active components are added during the first stage, then it may be preferred to calcine the first stage, and simply dry the second stage after the additional silica is added.

Where some of the active components are added in the second stage, then calcining is necessary to produce the active phase of the catalyst.

Calcining of the first stage will depend on the amount of surface area desired in the final catalyst. For a high surface area catalyst, the first stage should be calcined, with the second stage receiving a mild heat treatment. For lower surface area, calcining should be delayed till the second stage preparation is complete.

After the first stage has been dried and possibly calcined, the second stage addition is accomplished along with any additional active component desired. The silica used in this second addition can be silica sol, silica gel, diatomaceous earth or any precursor to silica such as silicate that preferably has a surface area of 50 m²/g or more. These silicas are known in the art for use as catalyst supports. While some fumed silica can be added at this time, there has to be some other form of silica also. The addition of silica in the second stage preparation should be in the form of a slurry or solution.

The method of adding other active components to the catalyst can be the same as found in the first stage.

After the second silica addition has been made, the catalyst is then dried in a manner similar to the first stage drying. If a fluid-bed catalyst is desired, the drying should be by spray drying.

Calcining of this final catalyst will depend upon the parameters set forth above in discussing the calcining of the first stage.

Using the present invention, the final percent active components in the supported catalyst can be as high as 90% with 50-80% being preferred. For example, a 70% active component, 30% silica catalyst can be prepared from a first stage 85% active-15% silica solution, with the remaining silica being added in the second stage. Thus a higher percent active component phase in the catalyst can be used, with the catalyst still having good physical properties.

It has also been found that the present invention gives enhanced porosity to fluid-bed catalysts, which should give greater stability and life to the catalysts during the reaction.

COMPARATIVE EXAMPLE A AND EXAMPLE 1

Catalysts were prepared in a two-stage manner. Comparative Example A utilized silica sol in both steps, while fumed silica was used in the first stage of Example 1.

Comparative Example A catalyst, being 70% ($K_{0.2}Ni_{2.8}-Co_{5.2}Fe_2Bi_{1.67}P_{1.0}Mo_{12}O_x$), 30% $SiO_2$ was prepared as follows. A first-stage catalyst of 85% active component and 15% silica was prepared by first preforming bismuth molybdate. $H_3PO_4$ was then added to a 40% silica sol and stirred for 4 minutes. To this was added metal nitrates of Fe, Ni, Co and K. After 10 minutes, $(NH_4)_6Mo_7O_{24}\cdot 6H_2O$ was added followed by the preformed bismuth molybdate. The resulting yellow slurry was mixed by stirring at a temperature of about 52° C. After 5 hours, the slurry was then spray dried. For the second stage, three thousand grams of this first stage, 1,607 grams of 40% silica sol and 3,000 cc of water were mixed together. The slurry was ball milled for 20 hours, and then spray dried. After drying, the catalyst was calcined at 550° C. for one hour, 580° C. for 4 hours, and 600° C. for 2 hours.

Example 1 catalyst, having the same percentages carrier and active components of Comparative Example A, but with the silica being 15% fumed silica and 15% silica sol, was prepared as follows:

A first-stage catalyst of 85% active phase and 15% fumed silica was prepared by first preforming bismuth molybdate. $H_3PO_4$ and water were added to about a third of the silica and stirred. To this was added metal nitrate of Fe, Ni, Co and K, also dissolved in water. About one-third of the fumed silica was added to this nitrate-containing solution and stirred for 10 minutes. $(NH_4)_6Mo_7O_{24}\cdot 6H_2O$, the preformed bismuth molybdate, and the rest of the fumed silica was then added to this solution. The resulting yellow slurry was stirred overnight at a temperature of 52° C. After stirring, the batch was spray dried.

To 3,000 grams of the first stage, 1,607 grams of 40% silica sol and 3,000 grams of water were added. The slurry was ball milled for 20 hours, and then spray dried. After drying, the catalyst was calcined at 550° C. for one hour, 580° C. for four hours, and 600° C. for two hours.

The above catalysts were tested in a 1¼ inch S.T. fluid-bed reactor operating at 22 psig. A mixture of propylene/air/nitrogen in a ratio of 1/8/3 was passed over the respective catalyst at a WWH of 0.064. The results are presented in Table I.

TABLE I

| | Preparation of Acrolein and Acrylic Acid | | | | | |
|---|---|---|---|---|---|---|
| | Temp. | Conver- | Single Pass Yield | | | Attri- |
| Example | °C. | sion | Acrolein | AA | Both | tion |
| Comp. Ex. A | 348 | 92.7 | 72.6 | 9.1 | 81.7 | 10 |
| Example 1 | 342 | 95.4 | 76.2 | 8.6 | 84.8 | 6.4 |

As can be seen above, catalysts containing fumed silica achieve higher total conversions and higher single pass yields to the desired product. Further, the attrition number of the catalysts containing fumed silica is significantly lower than that of Comparative Example A. The lower the attrition number, the greater strength of the catalyst. In addition, the surface area of Example 1 catalyst was measured to be 14.6 m²/g, whereas Comparative Example A catalyst surface area was only 6.7 m²/g.

EXAMPLES 2-4—Effect of Water and Nitrogen

To further show the uniqueness of the present invention's catalyst, catalysts prepared in the conventional manner for the oxidation of propylene can be enhanced in selectivity by the addition of water during the reaction. Catalysts prepared by the present invention, however, show a decrease in performance with water addition. Higher yields can be achieved by using an inert gas or recycle such as nitrogen instead of water. This is an unexpected advantage of the present invention, for it decreases the amount of water that must be removed in the final reactor effluent. The following examples show this advantage.

A catalyst having the same percentage active phase and fumed silica-sol as found in Example 1 was prepared. This catalyst was then tested in the reactor of Example 1 for the conversion of propylene to acrolein and acrylic acid. A mixture of propylene/air in a ratio of 1/8 was passed over the catalyst. Example 2 shows the effect of using three parts water as a diluent. In Example 3, the water was replaced with three parts nitrogen, and Example 4 was run without any diluent. The results are presented in Table II.

TABLE II

Effect of N₂ and H₂O Addition

| Example | Diluent | Temp °C. | Conversion | Single Pass Yield Acrolein | AA | Both |
|---|---|---|---|---|---|---|
| 2 | H₂O | 349 | 96.1 | 66.7 | 16.9 | 83.6 |
| 3 | N₂ | 343 | 95.7 | 73.9 | 12.2 | 86.1 |
| 4 | O | 350 | 96.9 | 68.5 | 15.2 | 83.7 |

As can be seen above, the addition of water actually decreases the single pass yield to acrolein and the total single pass yield to acrolein and acrylic acid over that that can be achieved without any diluent. The use of nitrogen, however, actually shows an increase in the yields of acrolein and acrylic acid over either no diluent addition or the use of water.

The source of nitrogen can be external to the process involved, or can be recycle gas recovered from processing of the reactor effluent. For example, the process for producing acrylic acid can consist of two reactors, a first stage for the conversion of propylene to acrolein and a second stage to convert acrolein to acrylic acid. The inert gases containing nitrogen leaving the second stage can be recovered and recycled back to the first, second or both stages of the reaction.

We claim:

1. In the process for the preparation of unsaturated aldehydes and acids from propylene or isobutylene by the vapor phase oxidation of propylene or isobutylene with molecular oxygen and nitrogen at a temperature of about 200°-600° C. in the presence of a supported solid oxide complex catalyst the improvement comprising preparing said catalyst by the steps of:

(a) adding fumed silica to a mixture containing one or more active components of the catalyst;
(b) drying and calcining said mixture to form a calcined first-stage mixture; said calcination occurring between the temperature of 200°-700° C.
(c) adding in solution a member having a surface area greater than 50 m²/g selected from the group of silica and a silica-containing compound other than fumed silica to said calcined mixture of (b);
(d) drying said mixture of (c).

2. In the process for the preparation of unsaturated aldehydes and acids from propylene or isobutylene by the vapor phase oxidation of propylene or isobutylene with molecular oxygen at a temperature of about 200°-600° C. in the presence of a supported solid oxide complex catalyst the improvement comprising preparing said catalyst by the steps of:

(a) adding fumed silica to a mixture containing one or more active components of the catalyst;
(b) drying and calcining said mixture to form a calcined first-stage mixture; said calcination occurring between the temperature of 200°-700° C.;
(c) adding in solution a member having a surface area greater than 50 m²/g selected from the group of silica and a silica-containing compound other than fumed silica to said calcined mixture of (b);
(d) drying said mixture of (c).

3. The process of claims 1 or 2 wherein during step (c) of the catalyst preparation, one or more active components of the catalyst are additionally added to the solution, and wherein after drying step (d), the catalyst is calcined at a temperature between 200°-700° C.

* * * * *